(12) United States Patent
Patton et al.

(10) Patent No.: US 7,879,573 B2
(45) Date of Patent: Feb. 1, 2011

(54) ISOLATION OF ANALYTES

(75) Inventors: Wayne Forrest Patton, Newton, MA (US); Thomas Edwin Miller, Boston, MA (US); Nan Fei Jiang, Newton, MA (US); Michael Paul O'Malley, Tyngsboro, MA (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 343 days.

(21) Appl. No.: 11/772,739

(22) Filed: Jul. 2, 2007

(65) Prior Publication Data

US 2008/0026408 A1    Jan. 31, 2008

Related U.S. Application Data

(60) Provisional application No. 60/818,183, filed on Jun. 30, 2006.

(51) Int. Cl.
*G01N 33/566* (2006.01)
(52) U.S. Cl. ......................................... 435/7.5; 436/501
(58) Field of Classification Search ........................ None
See application file for complete search history.

(56) References Cited

U.S. PATENT DOCUMENTS

2005/0059117 A1    3/2005    Rosen et al.
2005/0089930 A1    4/2005    Schneider et al.

OTHER PUBLICATIONS

Orr, "The Use of the 2-Iminobiotin-Avidin Interaction for the Selective Retrieval of Labeled Plasma Membrane Components," J. of Biol. Chem. 256(2):761-766, (1981).

Jacob et al., "Surface and Intracellular Distribution of a Putative Neuronal Nicotinic Acetylcholine Receptor," J. of Cell Biol. 103:205-214, (1986).

Twyman, "Two-dimensional polyacrylamide gel electroporesis," retrieved on Aug. 2003, <http://genome.wellcome.ac.uk/doc_wtd021045.html>.

*Primary Examiner*—Robert A Zeman
(74) *Attorney, Agent, or Firm*—Fish & Richardson P.C.

(57) ABSTRACT

The disclosure features, inter alia, methods and compositions for detecting, isolating, and/or analyzing one or more analytes such as, but not limited to, biomolecules (e.g., proteins, glycoproteins, lipids (e.g., sphingolipids), and carbohydrates). Such methods and compositions are useful in, e.g., the discovery of novel proteins, or the amino acid sequence of novel proteins, or identifying biomarkers for diseases such as cancer, immunological disorders, or microbial infections.

30 Claims, 3 Drawing Sheets

ISOLATION OF ANALYTES

CROSS-REFERENCE TO RELATED APPLICATIONS

This application claims priority to U.S. application Ser. No. 60/818,183, filed Jun. 30, 2006, the contents of which are hereby incorporated by reference.

SUMMARY

The disclosure relates to, inter alia, detecting, isolating, and/or analyzing an analyte such as, but not limited to, a biomolecule (e.g., a protein, a glycoprotein, a lipid (e.g., a sphingolipid), and a carbohydrate). For example, this disclosure features methods and compositions useful for isolating an analyte from a mixture.

The methods and compositions described herein have a variety of applications and can be used, e.g., to detect the presence or amount of one or more cell-surface proteins or to analyze one or more cell-surface proteins. Such methods are useful in, e.g., the discovery of new proteins, or elucidating the amino acid sequence of new proteins, such as proteins involved in cancer, immunological disorders, microbial infections, metabolic disorders, or other disease states.

In one aspect, the disclosure features a method for isolating an analyte from a mixture. The method includes the steps of: providing an iminobiotin marker-conjugated analyte, wherein the iminobiotin marker-conjugated analyte has been separated from a mixture using a separation matrix and wherein the iminobiotin marker-conjugated analyte in the separation matrix has been labeled with a detectable biotin-binding molecule under conditions sufficient for the detectable biotin-binding molecule to bind to iminobiotin with high affinity; isolating the iminobiotin marker-conjugated analyte from the separation matrix; and removing the detectable biotin-binding molecule from the iminobiotin marker-conjugated analyte under conditions that decrease the binding affinity of the biotin-binding molecule for iminobiotin. In some embodiments, more than one (e.g., at least two, at least three, at least four, at least five, at least six, at least seven, at least eight, at least nine, at least 10, at least 11, at least 12, at least 15, at least 20, at least 30, at least 40, at least 50, at least 60, at least 70, at least 80, at least 90, at least 100, at least 200, at least 500, at least 1000, at least 2000, at least 5000, at least 10000, or at least 20000 or more) iminobiotin marker-conjugated analyte(s) can be provided.

In another aspect, the disclosure features a method for isolating an analyte from a mixture. The method includes the steps of: providing a mixture comprising an iminobiotin marker-conjugated analyte; separating the iminobiotin marker-conjugated analyte from the mixture using a separation matrix; labeling the iminobiotin marker-conjugated analyte in the separation matrix with a detectable biotin-binding molecule, wherein the labeling occurs under conditions sufficient for the biotin-binding molecule to bind to iminobiotin with high affinity; isolating the iminobiotin marker-conjugated analyte from the separation matrix; and removing the detectable biotin-binding molecule from the iminobiotin marker-conjugated analyte under conditions that decrease the binding affinity of the biotin-binding molecule for iminobiotin. In some embodiments, the mixture can contain more than one (e.g., at least two, at least three, at least four, at least five, at least six, at least seven, at least eight, at least nine, at least 10, at least 11, at least 12, at least 15, at least 20, at least 30, at least 40, at least 50, at least 60, at least 70, at least 80, at least 90, at least 100, at least 200, at least 500, at least 1000, at least 2000, at least 5000, at least 10000, or at least 20000 or more) iminobiotin marker-conjugated analyte(s).

In another aspect, the disclosure provides a method for isolating an analyte from a mixture, which method includes the steps of: conjugating an iminobiotin marker to an analyte in a mixture; separating the iminobiotin marker-conjugated analyte from the mixture using a separation matrix; labeling the iminobiotin marker-conjugated analyte in the separation matrix with a detectable biotin-binding molecule, wherein the labeling occurs under conditions sufficient for the biotin-binding molecule to bind to iminobiotin with high affinity; isolating the iminobiotin marker-conjugated analyte from the separation matrix; and removing the detectable biotin-binding molecule from the iminobiotin marker-conjugated analyte under conditions that decrease the binding affinity of the biotin-binding molecule for iminobiotin. In some embodiments, the iminobiotin marker can be conjugated to more than one (e.g., at least two, at least three, at least four, at least five, at least six, at least seven, at least eight, at least nine, at least 10, at least 1, at least 12, at least 15, at least 20, at least 30, at least 40, at least 50, at least 60, at least 70, at least 80, at least 90, at least 100, at least 200, at least 500, at least 1000, at least 2000, at least 5000, at least 10000, or at least 20000 or more) analyte(s).

In another aspect, the invention provides a method for isolating an analyte from a mixture. The method includes conjugating an iminobiotin marker to an analyte in the mixture; resolving the iminobiotinylated analyte in the mixture by gel electrophoresis; labeling the gel-resolved iminobiotinylated analyte with a labeled biotin-binding molecule under basic conditions, wherein the detectable biotin-binding molecule is conjugated to a detectable label, optionally excising the labeled iminobiotinylated analyte from the gel; and removing the label from the iminobiotinylated analyte under acidic conditions. In some embodiments, the iminobiotin marker can be conjugated to more than one (e.g., at least two, at least three, at least four, at least five, at least six, at least seven, at least eight, at least nine, at least 10, at least 11, at least 12, at least 15, at least 20, at least 30, at least 40, at least 50, at least 60, at least 70, at least 80, at least 90, at least 100, at least 200, at least 500, at least 1000, at least 2000, at least 5000, at least 10000, or at least 20000 or more) analyte(s).

In yet another aspect, the disclosure features a method for isolating an analyte from a mixture. The method includes the steps of: conjugating an iminobiotin marker to an analyte at the surface of a cell; preparing a mixture from the cell; separating the iminobiotin marker-conjugated analyte from the mixture using a separation matrix; labeling the iminobiotin marker-conjugated analyte in the separation matrix with a detectable biotin-binding molecule, wherein the labeling occurs under conditions sufficient for the biotin-binding molecule to bind to iminobiotin with high affinity; isolating the iminobiotin marker-conjugated analyte from the separation matrix; and removing the detectable biotin-binding molecule from the iminobiotin marker-conjugated analyte under conditions that decrease the binding affinity of the biotin-binding molecule for iminobiotin. In some embodiments, the iminobiotin marker can be conjugated to more than one (e.g., more than two, more than three, more than four, more than five, more than six, more than seven, more than eight, more than nine, more than 10, more than 11, more than 15, more than 20, more than 30, more than 50, more than 100, more than 200, more than 500, more than 1000, more than 2000, more than 5000, more than 10000, or more than 20000 or more) analyte(s) at the surface of a cell.

In yet another aspect, the disclosure features a method for analyzing an iminobiotin marker-conjugated analyte. The method can include the steps of: providing an iminobiotin marker-conjugated analyte, wherein the iminobiotin marker-conjugated analyte has been separated from a mixture using a separation matrix, wherein the iminobiotin marker-conjugated analyte has been labeled with a detectable biotin-binding molecule under conditions sufficient for the biotin-binding molecule to bind to iminobiotin with high affinity, and wherein the iminobiotin marker-conjugated analytes has been isolated from the separation matrix; removing the detectable biotin-binding molecule from the iminobiotin marker-conjugated analyte under conditions that decrease the binding affinity of the biotin-binding molecule for iminobiotin; and analyzing the iminobiotin marker-conjugated analyte. The analyzing can include, for example, mass spectrometry.

In another aspect, the disclosure features a methods for analyzing a surface protein, which method can include the steps of: conjugating an iminobiotin marker to a cell-surface protein; preparing a mixture from the cell; concentrating the iminobiotin marker-conjugated cell-surface protein; separating the concentrated iminobiotin marker-conjugated cell-surface protein using gel electrophoresis; labeling the iminobiotin marker-conjugated cell-surface protein with a detectable biotin-binding molecule, wherein the labeling occurs under conditions sufficient for the detectable biotin-binding molecule to bind to iminobiotin with high affinity; removing the detectable biotin-binding molecule from the iminobiotin marker-conjugated cell-surface protein under conditions that decrease the binding affinity of the biotin-binding molecule to iminobiotin; isolating the iminobiotin marker-conjugated cell-surface protein from the separation matrix; and analyzing the isolated iminobiotin marker-conjugated cell-surface protein using mass spectrometry.

In some embodiments of any of the methods described above, more than one iminobiotin marker-conjugated analyte can be isolated from the separation matrix and/or the detectable biotin-binding molecule can be removed from more than one iminobiotin marker-conjugated analyte.

In some embodiments of any of the methods described above, isolating the iminobiotin marker-conjugated analyte from the separation matrix can occur prior to removing the detectable biotin-binding molecule from the iminobiotin marker-conjugated analyte under conditions that decrease the binding affinity of the biotin-binding molecule for iminobiotin. In some embodiments, removing the detectable biotin-binding molecule from the iminobiotin marker-conjugated analyte under conditions that decrease the binding affinity of the biotin-binding molecule for iminobiotin can occur prior to isolating the iminobiotin marker-conjugated analyte from the separation matrix.

In some embodiments of any of the methods described above, the conditions sufficient for the biotin-binding molecule to bind to iminobiotin with high affinity can be basic conditions. In some embodiments, the conditions that decrease the binding affinity of the biotin-binding molecule to iminobiotin can be acidic conditions and/or conditions under which there is competition for binding for the detectable biotin-binding molecule (e.g., the presence of a free biotin or iminobiotin competitor).

In some embodiments of any of the methods described above, the separating can include, or consist of, resolving the iminobiotin marker-labeled analytes in one dimension or two dimensions. The separation matrix can be an acrylamide gel, an agarose gel, or a thin layer chromatography plate.

In some embodiments, any of the methods described above can further include the step of concentrating the iminobiotin marker-conjugated analyte. The concentrating can occur before separating the iminobiotin marker-conjugated analyte from the mixture using the separation matrix. The concentrating can include contacting the mixture with a biotin-binding column.

In some embodiments of any of the methods described above, the detectable biotin-binding molecule can be conjugated to a detectable label. The detectable label can be enzymatically active, fluorescent, colorimetric, or luminescent. The biotin-binding molecule can include, or consist of, neutravidin, captavidin, streptavidin, or avidin.

In some embodiments of any of the methods described above, the analyte to which the iminobiotin marker is conjugated can be a lipid or a polypeptide. The polypeptide can be a cell-surface polypeptide such as, but not limited to, a receptor (e.g., a receptor tyrosine kinase, a G protein-coupled receptor, a death receptor, or a cytokine receptor). The polypeptide can be a viral polypeptide, e.g., a viral surface polypeptide or a viral protein expressed on the surface of a host cell. The polypeptide can be modified. For example, the analyte (e.g., the polypeptide) can be phosphorylated, ubiquitinated, SUMOylated, or glycosylated.

In some embodiments, any of the methods described above can further include the step of, after separating the iminobiotin marker-conjugated analyte from the mixture using a separation matrix, fixing the iminobiotin marker-conjugated analyte in the separation matrix with a fixing agent. The fixing agent can be, e.g., isopropanol or methanol. The fixing agent can be in solution, for example, a solution of isopropanol in water.

In some embodiments, any of the methods described above can further include the step of: (i) after labeling the iminobiotin marker-conjugated analyte with a detectable biotin-binding molecule, detecting the iminobiotin marker-conjugated analyte and/or (ii) analyzing the isolated iminobiotin marker-conjugated analyte. The analyzing can include, or consist of, mass spectrometry (e.g., tandem mass spectrometry). The analyzing can include, e.g., contacting the isolated iminobiotin marker-conjugated analyte with a protease. Analyzing can include detecting if the iminobiotin marker-conjugated analyte is modified (e.g., phosphorylated, ubiquitinated, SUMOylated, or glycosylated) by, e.g., contacting the iminobiotin marker-conjugated analyte with a phosphate-binding moiety.

In some embodiments, any of the methods described herein can further include the step of, after separating the iminobiotin marker-conjugated analyte from the mixture, determining the amount of iminobiotin marker-conjugated analyte. The determining can include, e.g., determining the total amount of analytes in the mixture. Where the analyte is a polypeptide, the determining can include contacting the separation matrix (or some or all of the analytes (e.g., iminobiotin marker-conjugated analytes or non-conjugated analytes) contained in the separation matrix) with a protein staining agent. The protein staining agent can be silver nitrate or Coomassie blue or any other described herein.

In some embodiments of any the methods described herein, the mixture can be a cell lysate. The mixture can be a membrane fraction, a cytosolic fraction, a cytoskeleton fraction, or a nuclear fraction of a cell lysate. The mixture can be a plasma fraction of blood.

In some embodiments of any of the methods described herein, the iminobiotin marker can be conjugated to an analyte (e.g., a polypeptide or a lipid) at the surface of a cell. The methods can thus further include the step of, after conjugating the iminobiotin marker to the analyte, preparing a mixture from the cell.

In yet another aspect, the disclosure features a kit (e.g., useful in isolating, detecting, and/or analyzing an analyte). The kit can include: an iminobiotin marker; a detectable biotin-binding molecule; and instructions for conjugating an iminobiotin marker to an analyte. The kit can also include one or more solutions for removing a biotin-binding molecule from an iminobiotin marker and/or instructions for removing a biotin-binding molecule from an iminobiotin marker. The one or more solutions for removing a biotin-binding molecule from an iminobiotin marker can have an acidic pH and/or contain a free biotin or iminobiotin marker competitor. The kit can also, optionally, include instructions for detecting the detectable label. The iminobiotin marker can be an amine reactive iminobiotin marker such as NHS-iminobiotin. The detectable biotin-binding molecule can be conjugated to a detectable label. For example, the detectable label can be enzymatically active, fluorescent, colorimetric, or luminescent. The biotin-binding molecule can be neutravidin, captavidin, streptavidin, or avidin.

In some embodiments, the kit can include one or more control analytes. At least one of the one or more control analytes can be conjugated to an iminobiotin marker. At least one or more one or more control analytes is not conjugated to an iminobiotin marker. The kit can include at least two (e.g., at least three, at least four, at least five, at least six, or at least seven or more) control analytes. The control analyte(s) can be a polypeptide such as, but not limited to, serum albumin (e.g., human serum albumin or bovine serum albumin).

In some embodiments, the kit can further include one or more buffers. The buffers can have a basic or acidic pH.

In some embodiments, the buffers and/or solutions contained in the kit do not contain detectable levels of primary amines, e.g., as determined by Bradford assay.

In some embodiments, the kit can include an amino acid such as glycine.

In yet another aspect, the disclosure provides a method for detecting one or more analytes in a mixture. The method includes the steps of: providing a mixture comprising one or more analytes conjugated to an iminobiotin marker; contacting the iminobiotin marker-conjugated analytes to a plurality of analyte-capturing agents, wherein the plurality comprises at least two different analyte-capturing agents, and wherein each of the at least two different analyte-capturing agents specifically bind to a different analyte; and contacting the iminobiotin marker-conjugated analytes with a detectable biotin-binding molecule, wherein the binding of the detectable biotin-binding molecule to an iminobiotin marker-conjugated analyte indicates the presence of the analyte in the mixture. At least one (or all of the) analytes can be a protein or a lipid or any other analytes described herein. At least one or the analyte-capturing agents can be, e.g., an antibody. The method can further include the step of conjugating an iminobiotin marker to the one or more analytes. The method can further include the step of removing the biotin-binding molecule from at least one of the one or more iminobiotin marker-conjugated analytes under acidic conditions that decrease the binding affinity of the biotin-binding molecule to iminobiotin and/or determining if one or more of the analytes are modified. The modification can be phosphorylation, ubiquitination, or glycosylation. The determining if one or more analytes are modified can include contacting the iminobiotin marker-conjugated analyte with a phosphate-binding moiety.

In some embodiments, the analyte-capturing agents can be bound to a solid support such as a chip or a particle. The analyte-capturing agents can be bound to encoded and/or magnetic particles.

In yet another aspect, the disclosure features a kit containing a plurality of analyte-capturing agents, wherein the plurality comprises at least two different analyte-capturing agents, and wherein each of the at least two different analyte-capturing agents specifically bind to a different analyte; an iminobiotin marker; a detectable biotin-binding molecule; and instructions for detecting the detectable biotin-binding molecule. The plurality of analyte-capturing agents is bound to a solid support. At least one (or all) of the analyte-capturing agents can be an antibody.

Other features and advantages of the disclosure will be apparent from the following description, from the drawings, and from the claims.

BRIEF DESCRIPTION OF THE DRAWINGS

FIG. 3 is a pair of pictures of acrylamide gels depicting the patterns of subcellular fractions of cells whose proteins were conjugated with iminobiotin and either labeled with Ember™ Biotin Binder Dye (top picture) or counter-stained for total protein using SYPRO® Ruby protein gel stain (bottom picture). Human A431 cells (left side of the gel) and HEK293 cells (right side of the gel) were labeled for one hour at room temperature and fractionated using the Cellular Protein Fractionation kit (PerkinElmer Cat. # PRD101A001KT; PerkinElmer, Waltham, Mass.). Lane 1 contains gel-separated biotinylated molecular weight markers; Lane 2 contains gel-separated cytosolic fractions that did not contain iminobiotinylated proteins; Lane 3 contains gel-separated cytosolic fractions that do contain iminobiotinylated proteins; Lane 4 contains gel-separated membrane fraction without iminobiotinylated proteins; Lane 5 contains gel-separated membrane fractions with iminobiotinylated proteins; Lane 6 contains a gel-separated cytoskeletal fraction containing biotinylated proteins; Lane 7 contains a gel-separated positive control iminobiotinylated protein (A) and a control non-iminobiotinylated protein.

DETAILED DESCRIPTION

The disclosure features a variety of methods and compositions useful for detecting, isolating, and/or analyzing an analyte. The methods and compositions can be used, e.g., to detect (or analyze) abnormal protein modification (e.g., phosphorylation, ubiquitination, SUMOylation, or glycosylation), which abnormal modification can underlay a variety of disease states such as cancer, diabetes, inflammatory disorders, or metabolic disorders. Thus, the methods and compositions described herein can be used to identify biomarkers of disease and/or potential targets for rational drug design.

Figure 1:
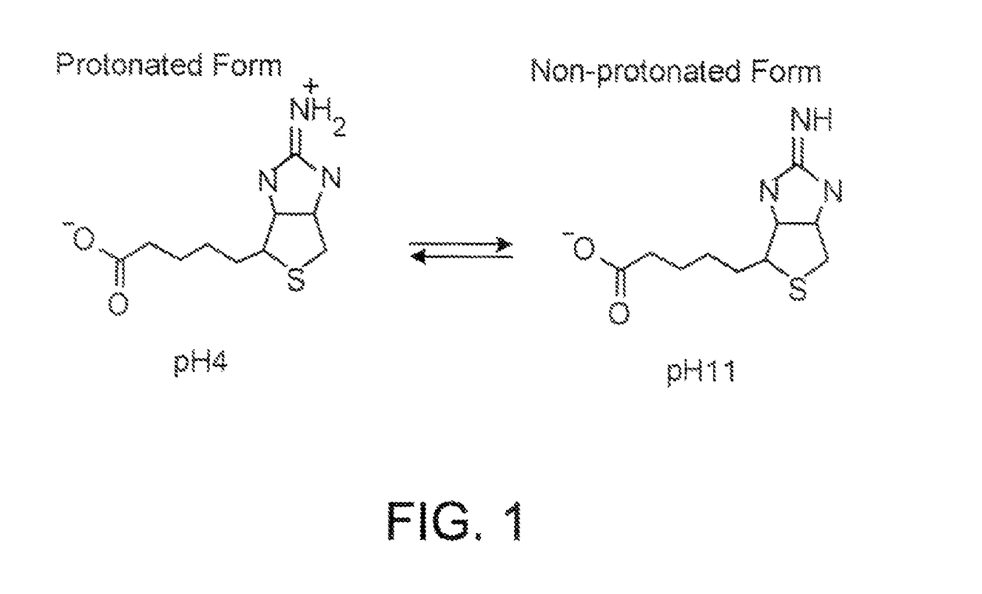
FIG. 1 is a schematic diagram depicting the protonation state of the 2-iminobiotin molecule at low and high pH.

In some embodiments, the methods described herein can include the step of conjugating an iminobiotin marker to an analyte in a mixture. Iminobiotin is a low molecular weight compound which can be conjugated to many proteins, peptides, glycoproteins, and amino acids by a variety of reaction chemistries. The high-affinity binding of iminobiotin to avidin, streptavidin, and related biotin-binding molecules and the inherent signal amplification of the biotin-avidin system has made it useful for a wide variety of immunological and other protein-based methodologies. One advantage of iminobiotin, as compared to a related molecule biotin, is that unlike the biotin/biotin-binding molecule interaction that it is essentially irreversible under physiological conditions (e.g., avidin has a strong affinity with biotin ($Ka=10^{15}$ $M^{-1}$)), the iminobiotin/biotin-binding molecule interactions are reversible (e.g., are pH dependent). For example, avidin also forms a complex with 2-iminobiotin, the cyclic guanidino analog of biotin ($Ka=10^8$ $M^{-1}$ at pH 9.5), however, the binding of avidin or streptavidin to 2-iminobiotin is pH-dependent, wherein affinity decreases as the pH is lowered. Thus, at high pH values, the free base form of 2-iminobiotin retains the high affinity selective avidin binding property of biotin, whereas an acidic pH values converts 2-iminobiotin to a salt form that interacts poorly (has reduced affinity) with avidin. The protonation states of 2-iminobiotin at acidic and basic pH are shown in FIG. 1.

Conventional biotinylation of a lysine residue blocks the epsilon amino group of the labeled lysine on proteins, thereby significantly perturbing the protein's isoelectric point. Thus, another characteristic of iminobiotin conjugation, as compared to biotin conjugation, of proteins is that the positive charge of the amino group (e.g., the amino group of a lysine residue) is regenerated upon reaction of NHS-iminobiotin with polypeptides (Patton et al. (1989) Anal. Biochem. 256: 761-766). Thus, the conjugating of iminobiotin does not result in, e.g., a significant alteration in the isoelectric point of a protein used for isoelectric focusing separations (IEF; e.g., in a separation matrix). The conjugation reaction is also compatible with two-dimensional gel electrophoresis. It should be noted that the mass of the modified amino group increases by 225 daltons upon covalent modification with iminobiotin. While this increase in mass is too small to detect by polyacrylamide gel-electrophoresis (PAGE), the modification should be considered in analytical methods such as mass spectrometry (see below).

Applications (i) The disclosure features a variety of methods and compositions useful for detecting, isolating, and/or analyzing an analyte in a mixture. An analyte can be a molecule from any source. For example, the analyte can be a biomolecule such as, but not limited to, a protein, a nucleic acid, lipid (e.g., a sphingolipid), a fatty acid, a glycoprotein, or a saccharide or polysaccharide. A mixture can be any composition, e.g., a composition containing at least one analyte. In some instances, the mixture can be from a biological source including, without limitation, the lysate of a cell (or tissue), a particular compartment of a cell (e.g., the cytosolic, nuclear, or membrane fraction of a cell), or a plasma fraction from blood. The mixture can also be, e.g., a water sample, a food sample, or a sample of an unknown solvent.

Methods for isolating an analyte in a mixture can include the steps of: conjugating an iminobiotin marker to an analyte in a mixture; separating the iminobiotin marker-conjugated analyte from the mixture using a separation matrix; labeling the iminobiotin marker-conjugated analyte in the separation matrix with a detectable biotin-binding molecule, wherein the labeling occurs under conditions sufficient for the biotin-binding molecule to bind to iminobiotin with high affinity; isolating the iminobiotin marker-conjugated analyte from the separation matrix; and removing the detectable biotin-binding molecule from the iminobiotin marker-conjugated analyte under conditions that decrease the binding affinity of the biotin-binding molecule to iminobiotin.

Figure 2:
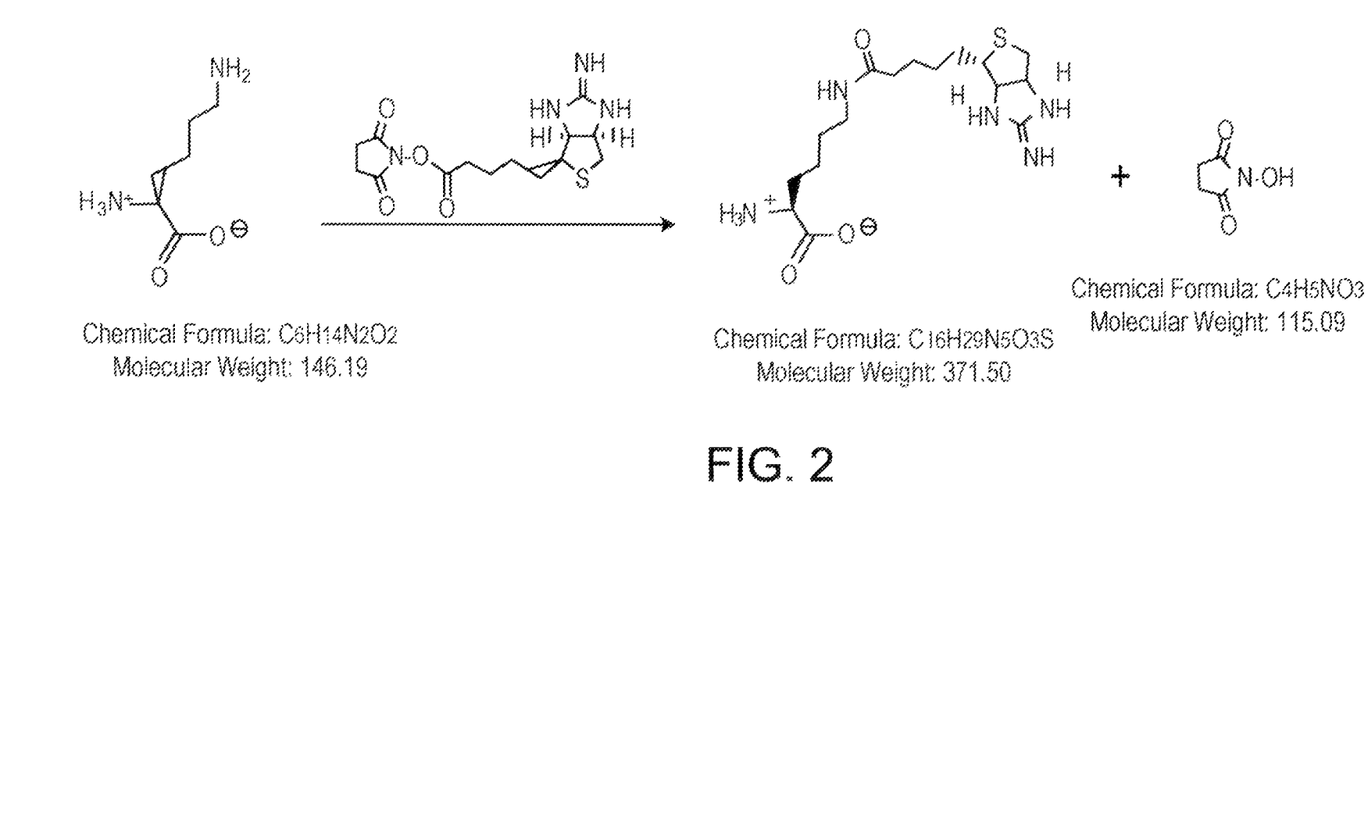
FIG. 2 is a schematic diagram depicting the chemical reaction of NHS-iminobiotin to the epsilon-amino group of lysine.

Methods for conjugating an iminobiotin marker to an analyte (such as a protein) are known in the art and detailed in the accompanying Examples. For example, where polypeptides or amino acids are to be conjugated to an iminobiotin marker, mixing the target polypeptides with NHS-ester activated iminobiotin marker (N-hydroxysuccinimidyl-iminobiotin trifluoroacetamide), e.g., allows for a spontaneous reaction to occur whereby the NHS on the NHS-iminobiotin marker reacts with an N-terminal amino group on the polypeptide or the amino acid (e.g., glycine) or an epsilon amino group of a lysine residue. The result is the addition of an iminobiotin marker to the polypeptide (i.e., the iminobiotinylation of the polypeptide). The conjugation of NHS-iminobiotin to lysine is depicted in FIG. 2. One exemplary reagent for use in conjugating an iminobiotin marker to an analyte is the EZ-link NHS (N-hydroxysuccinimidyl-iminobiotin trifluoroacetamide)-iminobiotin marker (Pierce Biotechnology Inc. (Rockland, Ill.)). Hydrazine and p-diazobenzoyl derivates of iminobiotin can be used to label oligosaccharides and tyrosine (or histidine) residues of proteins, respectively (see, e.g., Kinagwa et al. (1983) J. Biochem. 94(1160); Reisfeld et al. (1987) Biochem. Biophys. Res. Commun. 142:519; and Wilcheck et al. (1986) Biochem. Biophys. Res. Commun. 138:872, the disclosures of each of which are incorporated by reference in their entirety).

A mixture comprising one or more (e.g., two or more, three or more, four or more, five or more, six or more, seven or more, eight or more, nine or more, 10 or more, 15 or more, 20 or more, 30 or more, 40 or more, 50 or more, 100 or more, 200 or more, 500 or more, 1000 or more, 2000 or more, or 10,000 or more) analytes (e.g., proteins) of interest can be contacted with an iminobiotin marker, e.g., an amine reactive iminobiotin marker, and incubated for about one (e.g., about two, about three, about four, about five, about six, about seven, about eight, about nine, about 10, about 11, about 12, about 15, about 20, or about 24 or more) hours. The incubation can occur at, e.g., room temperature or 2-8° C. The reaction of an iminobiotin marker and one or more analytes in the mixture can be quenched by, e.g., the addition of a solution comprising an amino acid such as glycine (e.g., 100 mM glycine) to the mixture. Optionally, any remaining unreacted iminobiotin marker can be removed from the mixture, e.g., using dialysis techniques.

In some embodiments, more than one (e.g., more than two, more than three, more than four, more than five, more than six, more than seven, more than eight, more than nine, more than 10, more than 11, more than 15, more than 20, more than 30, more than 50, more than 100, more than 200, more than 500, more than 1000, more than 2000, more than 5000, more than 10000, or more than 20000 or more) analytes of interest can be conjugated to an iminobiotin-marker. In some embodiments, at least two (e.g., at least three, at least four, at least five, at least six, at least seven, at least eight, at least nine, at least 10, at least 11, at least 12, at least 15, at least 20, at least 30, at least 40, at least 50, at least 100, at least 200, at least 500, at least 1000, or at least 2000 or more) different analytes are conjugated to an iminobiotin-marker.

In some embodiments, the iminobiotin marker can be conjugated to one or more cell-surface proteins (e.g., cell-surface receptors such as G protein coupled receptors, cytokine receptors, death receptors (e.g., Fas receptor or TNF receptor), or tyrosine kinase receptors). For example, cells grown in a tissue culture vessel (e.g., a tissue culture flask or dish) can be washed (once or multiple times) with a buffer that does not contain primary amines (such as phosphate buffered saline) and, optionally, isolated from the tissue culture vessel (e.g., by trypsinization/EDTA treatment of adherent cells or centrifugation of suspension cells). The cells are then contacted with the iminobiotin marker, e.g., an amine reactive iminobiotin marker such as NHS-iminobiotin, for about one (e.g., about two, about three, about four, about five, about six, about seven, about eight, about nine, about 10, about 11, about 12, about 15, about 20, or about 24 or more) hours at, e.g., room temperature. The reaction can be quenched with the addition of a solution comprising an amino acid such as glycine.

Following conjugation of an iminobiotin marker to one or more cell-surface proteins, a mixture can be made from the cells. For example, a cell lystate mixture can be prepared from cells by contacting a cell sample with a lysis buffer including one or more detergents (e.g., saponin, sodium dodecyl sulfate, deoxycholine, NP-40, Tween-20, or Triton X-100). The buffer can also, optionally, include one or more reagents that preserve the integrity of iminobiotin marker-conjugated analytes. Such agents are well known to those skilled in the art and include, e.g., inhibitors (e.g., nuclease, protease, kinase, and phosphatase inhibitors) which preserve or minimize changes in the iminobiotin marker-conjugated proteins. Inhibitors include, for example, chelators such as ethylenediamne tetraacetic acid (EDTA), ethylene glycol bis(P-aminoethyl ether) N,N,N1,N1-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Appropriate buffers and conditions for isolating molecules are well known to those skilled in the art and can be varied depending, for example, on the type of molecule in the sample to be characterized (see, for example, Ausubel et al. Current Protocols in Molecular Biology (Supplement 47), John Wiley & Sons, New York (1999); Harlow and Lane, Antibodies: A Laboratory Manual (Cold Spring Harbor Laboratory Press (1988); Harlow and Lane, Using Antibodies: A Laboratory Manual, Cold Spring Harbor Press (1999); Tietz Textbook of Clinical Chemistry, 3rd ed. Burtis and Ashwood, eds. W. B. Saunders, Philadelphia, (1999)).

In some embodiments, a mixture can be processed to eliminate or minimize the presence of interfering substances. For example, a mixture can be fractionated or purified to remove one or more materials that are not of interest. Methods of fractionating or purifying a mixture (e.g., a protein mixture) include, but are not limited to, chromatographic methods such as liquid chromatography, ion-exchange chromatography, size-exclusion chromatography, or affinity chromatography.

In some embodiments, a cell lysate mixture can be fractionated to obtain one or more subcellular fractions of interest such as, e.g., cytosolic, nuclear, cytoskeletal, or membrane fractions. The fractionation methods can include, e.g., differential centrifugation. For example, a mixture can be passed through sucrose, Percoll, metrizamide, or Nycodenz gradients (rate zonal and isopycnic) to obtain a specific subcellular fraction.

In some embodiments, following the conjugation of an iminobiotin marker to an analyte (e.g., a protein) in a mixture (or preparation of a cell lysate mixture containing an iminobiotin marker-conjugated analyte), the iminobiotinylated analyte can be enriched (concentrated) by contacting the mixture with a biotin-binding column (e.g., an avidin- or streptavidin-affinity column). For example, streptavidin-agarose resin is suitable for isolating an iminobiotinylated analyte such as a protein. The bound iminobiotin marker-conjugated analyte can be removed from the column under conditions that decrease the binding affinity of the biotin-binding molecule for iminobiotin. The released iminobiotin marker-conjugated analyte is generally collected in a smaller volume than the original mixture such that its concentration is increased. Exemplary biotin-binding reagents useful for concentrating iminobiotin marker conjugated analytes include the High Capacity Streptavidin Coated Plate (PerkinElmer Cat. # 6006625, Waltham, Mass.).

Additional methods suitable for preparing a mixture from a cell sample are described in, e.g., Sambrook et al. Molecular Cloning: A Laboratory Manual Second Edition vol. 1, 2 and 3. Cold Spring Harbor Laboratory Press: Cold Spring Harbor, N.Y., USA, November 1989; the disclosure of which is incorporated herein by reference in its entirety.

Methods for separating at least one iminobiotin marker-conjugated analyte (e.g., a protein) using a separation matrix are detailed in the accompanying Examples. For example, a mixture containing an iminobiotin marker-conjugated analyte can be subjected to gel electrophoresis. In some embodiments, the gel is a cross-linked polymer whose composition and porosity is chosen based on the weight and composition of the analyte. One non-limiting gel of the invention is made of different concentrations of acrylamide and a cross-linker (e.g. N,N'-methylenebisacrylamide) that are induced to polymerize using agents such as tetramethylethylenediamine (TEMED) and/or ammonium persulfate to result in a meshed network of polyacrylamide. The pore size of the polyacrylamide gel can be altered by modifying the concentrations of the acrylamide and the cross-linker. In some embodiments, the acrylamide gel can include a denaturant such as sodium dodecyl sulfate or urea. Other non-limiting examples of a suitable separation matrix include an agarose gel or a thin layer chromatography (TLC) plate. The latter can be useful, e.g., where an analyte is a lipid or small molecule (e.g., a hydrophobic small molecule).

In some embodiments, the iminobiotinylated analyte can be separated in one dimension. In some embodiments, the iminobiotinylated analyte can be separated in a second direction (e.g., isoelectric focusing or two-dimensional gel electrophoresis). For example, a mixture of iminobiotinylated analytes can be separated by size in a first dimension and by charge (e.g., in a pH gradient) in a second dimension.

In some embodiments, following the separating, the analyte (e.g., a protein) can be fixed in the separation matrix. Fixation can include contacting the analyte or the separation matrix containing the analyte with a fixing agent (or solution containing a fixing agent). For example, an acrylamide gel containing both iminobiotinylated proteins can be contacted with a solution containing an alcohol such as isopropanol or methanol. A fixed gel can, optionally, be dried.

After the separation of an iminobiotin marker conjugated analyte (or, e.g., two or more, three or more, four or more, five or more, six or more, seven or more, eight or more, nine or more, 10 or more, 15 or more, 20 or more, 30 or more, 40 or more, 50 or more, 100 or more, 200 or more, 500 or more, 1000 or more, 2000 or more, 10000 or more, or all of the iminobiotin marker-conjugated analytes), can be labeled with a detectable biotin-binding molecule, e.g., under conditions sufficient for the detectable biotin-binding molecule to bind to iminobiotin with high affinity. The biotin-binding molecule can be, e.g., a neutravidin molecule, a captavidin molecule, an avidin molecule, or a streptavidin molecule, or an analog of any of the foregoing. A detectable biotin-binding molecule can be conjugated to one or more detectable labels. A detectable label can be directly detectable (e.g., fluorescent, radioactive (containing a radionuclide), luminescent, or colorimetric). A detectable label can also be indirectly detectable (e.g., recognizable by a specific antibody or enzymatically active (e.g., contains an active enzyme such as horseradish peroxidase, alkaline phosphatase, chloramphenicol acetyltransferase, or luciferase) such that it will convert a substrate into a detectable form. Fluorescent labels include, e.g., rhodamine, fluorescein, phycoerythrin (PE), PE-Cyanine-5.18, PE-Cyanine-3, allophycocyanin, and phycobiliproteins. Radionuclides can include, e.g., $^{33}P$, $^{32}P$, $^{125}I$, $^{35}S$, $^{14}C$, or $^3H$. In some embodiments, highly charged fluorophores containing sulfonate residues are not employed as a fluorescent label.

Conditions suitable for labeling an iminobiotin marker-conjugated analyte in a separation matrix with a detectable biotin-binding molecule with high affinity include, but are not limited to, basic conditions. Basic conditions include, e.g., conditions where the pH is greater than 7 (e.g., greater than 7.01, greater than 7.02, greater than 7.03, greater than 7.04, greater than 7.05, greater than 7.06, greater than 7.07, greater than 7.08, greater than 7.09, greater than 7.1, greater than 7.2, greater than 7.3, greater than 7.4, greater than 7.5, greater than 7.6, greater than 7.7, greater than 7.8, greater than 7.9, or greater than 8). In some embodiments, basic conditions are conditions where the pH is at least about 7.5 (e.g., at least about 7.6, at least about 7.7, at least about 7.8, at least about 7.9, or at least about 8 or more). In some embodiments, basic conditions are conditions where the pH is at least about 8.5 (e.g., at least about 8.6, at least about 8.7, at least about 8.8, at least about 8.9, or at least about 9.0 or more). In some embodiments, basic conditions are conditions where the pH is greater than about 9.0 (e.g., greater than about 9.1, greater than about 9.2, greater than about 9.3, greater than about 9.4, greater than about 9.5, greater than about 9.6, greater than about 9.7, greater than about 9.8, greater than about 9.9, or greater than 10 or more).

As used herein, "high affinity" refers to a high degree of attraction between two binding members (e.g., two atoms, two molecules, two macromolecules, or any combination thereof). In some embodiments, high affinity can be expressed in terms of an association constant (Ka) between two binding members. For example, two binding members can have a Ka of greater than or equal to about $10^5$ (e.g., about $10^6$, about $10^7$, about $10^8$, or about $10^9$ or greater) $M^{-1}$.

A non-limiting example of such a method for labeling an iminobiotin marker-conjugated analyte in a separation matrix (e.g., an iminobiotinylated protein in an acrylamide gel) with a detectable biotin-binding molecule is as follows. The proteins in the gel can be fixed with 50% isopropanol (in water) for 15 minutes. The fixing solution is removed and the fixed gel is then placed into an acidic solution (e.g., pH 10.5) containing a detectable biotin-binding molecule and incubated overnight at room temperature. Following the incubation, the gel can be washed with the acid solution either not containing the biotin-binding molecule or a reduced amount of the biotin-binding molecule.

Methods for removing a detectable biotin-binding molecule from an iminobiotin marker-conjugated analyte are detailed in the accompanying Examples. For example, an iminobiotin marker conjugated analyte bound to a detectable binding molecule can be incubated under conditions suitable for removing the detectable biotin-binding the iminobiotin marker-conjugated analyte, which include, e.g., acidic conditions; competition with biotin, iminobiotin, or a derivative thereof; or a combination of the foregoing. An iminobiotin marker conjugated analyte bound to a detectable binding molecule, or a separation matrix including the bound conjugates, can be incubated in a buffer with an acidic pH and/or free biotin, iminobiotin (or a derivative thereof). Acidic conditions include, e.g., conditions where the pH is less than 7 (e.g., less than 6.99, less than 6.98, less than 6.97, less than 6.96, less than 6.95, less than 6.94, less than 6.93, less than 6.92, less than 6.91, or less than 6.90 or less). In some embodiments, acidic conditions are conditions where the pH is less than about 6.5 (e.g., less than about 6.4, less than about 6.3, less than about 6.2, less than about 6.1, less than about 6.0 or less). In some embodiments, acidic conditions are conditions where the pH is less than about 5.5 (e.g., less than about 5.4, less than about 5.3, less than about 5.2, less than about 5.1, less than about 5.0 or less). In some embodiments, acidic conditions are conditions where the pH is less than about 5.0 (e.g., less than about 5.9, less than about 5.8, less than about 5.7, less than about 5.6, less than about 5.5, less than about 5.4, less than about 5.3, less than about 5.2, less than about 5.1, less than about 5.0, less than about 4.5, less than 4.0 or less than 3.5).

One non-limiting example of a method for removing a detectable biotin-binding molecule from an iminobiotinylated analyte is as follows. A section of a gel can be incubated in an acidic solution (pH 4.0) overnight at room temperature. The extent or completeness of the removal of the detectable biotin-binding molecule can be verified by detecting the presence of detectable biotin-binding molecules bound to iminobiotinylated analytes.

Isolation of an iminobiotin marker-conjugated analyte (or e.g., two or more, three or more, four or more, five or more, six or more, seven or more, eight or more, nine or more, 10 or more, 15 or more, 20 or more, 30 or more, 40 or more, 50 or more, 100 or more, 200 or more, 500 or more, 1000 or more, 2000 or more, 10000 or more, or all of the iminobiotin marker-conjugated analytes (whether labeled with the detectable biotin-binding molecule or not)) from a separation matrix can be accomplished by any suitable means. For example, an analyte can be isolated from the separation matrix by manually cutting (e.g., with a scalpel, knife, or shears) the analyte from the separation matrix (or a region of the separation matrix in which the analyte resides). The cutting can be performed by an automated "spot" picker (e.g., the PerkinElmer Life Sciences ProPic™ robotic spot picker). Another non-limiting method for isolating the iminobiotinylated analyte from the gel is to elute the iminobiotinylated analyte from the separation matrix by application of an electric field or subjecting the separation matrix (or small section of the matrix containing the analyte) to centrifugation.

In some embodiments, the detectable biotin-binding molecule can be removed from the iminobiotinylated analyte prior to isolating the iminobiotinylated analyte from the separation matrix. In some embodiments, the detectable biotin-binding molecule can be removed from the iminobiotinylated analyte after isolating the iminobiotinylated analyte from the separation matrix.

Figure 3:
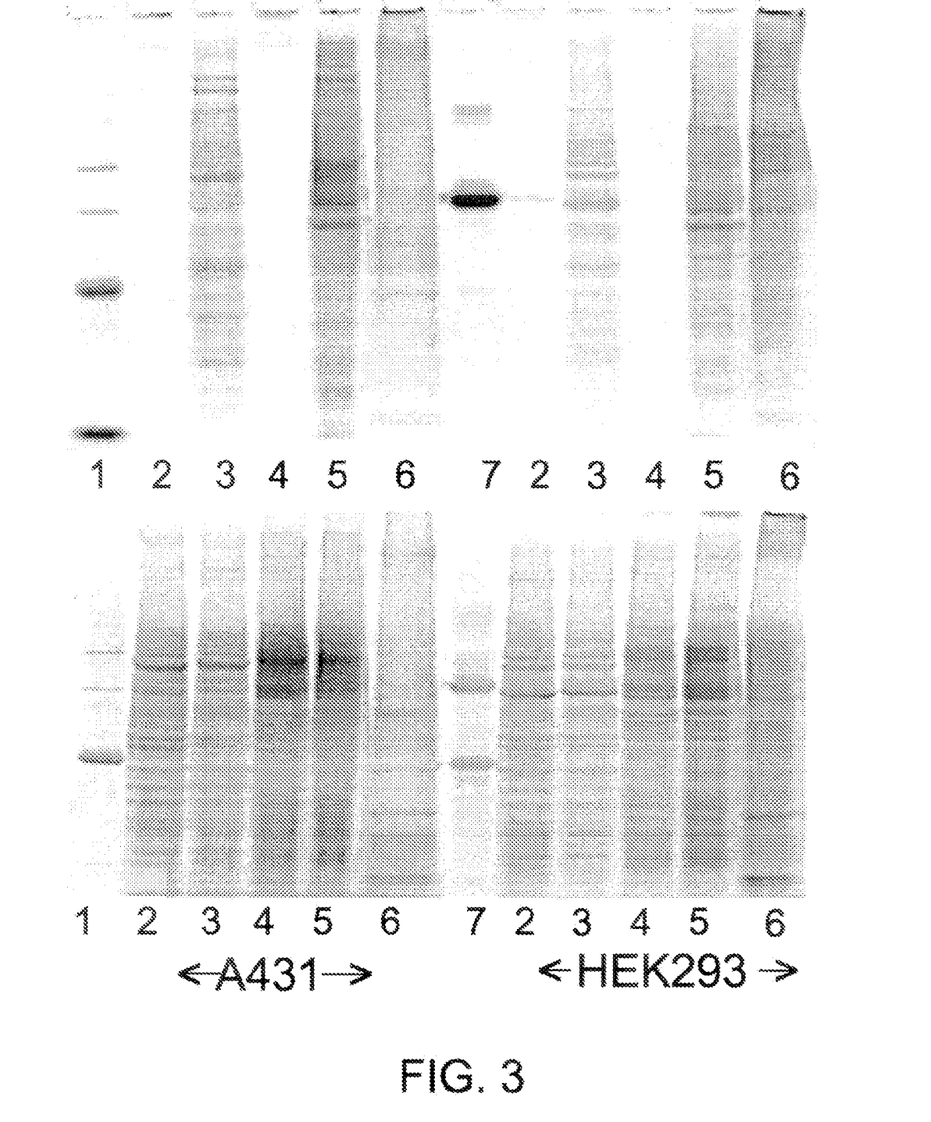

The isolation of an iminobiotin marker-conjugated analyte from a separation matrix can be aided by detecting or visualizing the iminobiotin marker-conjugated analyte. For example, the detectable biotin-binding molecule bound to the iminobiotinylated analyte can be detected and a portion of the separation matrix containing the iminobiotinylated analyte of interest can be removed. Methods of detecting the presence of and/or quantifying the amount of a detectable label depend on the nature of the label and are known in the art. Examples of detectors suitable for detecting such detectable labels include, without limitation, x-ray film, radioactivity counters, scintillation counters, spectrophotometers, colorimeters, fluorometers, luminometers, and densitometers. The presence of iminobiotinylated proteins labeled with a detectable biotin-binding molecule is shown in FIG. 3A.

In some embodiments, the separation matrix can be counter-stained such that both the iminobiotin marker-conjugated analyte and un-conjugated analytes are visible. For example, a polyacrylamide gel can be counter-stained with a protein dye such as Coomassie blue, SYPRO Ruby dye or silver stain (comprising silver nitrate). Such counter-staining procedures can be useful, e.g., in determining the concentration of the iminobiotin marker-conjugated analyte. For example, the relative amount of an iminobiotin marker-conjugated analyte can be compared to the amount of another analyte at a known concentration to thus determine the concentration of the iminobiotin marker-conjugated analyte. That is, the amount of an iminobiotin marker-conjugated protein visualized in a gel could be compared to the amount of a control un-conjugated protein (e.g., actin or tubulin) to thus determine the relative concentration of the iminobiotin marker-conjugated protein in the sample. A counter-stained gel containing both iminobiotinylated and non-biotinylated proteins is shown in FIG. 3B.

The methods can also include the step of analyzing the iminobiotin marker-conjugated analyte. Such analysis can, but does not necessary have to, occur after the iminobiotin marker-conjugated analyte has been removed from the separation matrix and the detectable biotin-binding molecule is removed. Methods of analyzing an iminobiotinylated protein include, e.g., matrix assisted laser desorption/ionization-time of flight-mass spectrometry (MALDI-TOF-MS)-based peptide mass fingerprinting or tandem mass spectrometry-based peptide sequencing and are described in, e.g., Clauser et al. (1995) Proc. Natl. Acad. Sci. USA 92:5072-5076; Dancik et al. (1999) J. Computation Biology 6(3//4):327-342; PCT Publication No. WO 07/015,690; and U.S. Pat. Nos. 5,049,507; 6,582,965; and 5,470,753, the disclosures of each of which are incorporated herein by reference in their entirety. Prior to analyzing (e.g., mass spectrometric analysis of) the iminobiotinylated analyte, the analyte can be contacted with a protease, e.g., trypsin. The analyte can be contacted with the protease prior to its isolation from the separation matrix (e.g., in-gel trypsinization) or after its separation from the matrix.

In some embodiments, the methods can also include the step of determining if the iminobiotin marker-conjugated analyte (e.g., a protein) contains a modification. The modification can be, e.g., phosphorylation, glycosylation, SUMOylation, or ubiquitination. The presence or absence of a phosphorylated residue (e.g., tyrosine, threonine, or serine) of a protein, e.g., can be determined by a variety of techniques including mass spectrometry, immunoassay (western blotting or enzyme-linked immnuosorbent assay (ELISA)), or contacting the protein with a phosphate-binding molecule such as, but not limited to, the Phos-tag™ reagent (PerkinElmer). Methods for detecting glycosylation can also include, e.g., mass spectrometry, immunoassay (western blotting or enzyme-linked immnuosorbent assay (ELISA)), or DNA sequencer-assisted (DSA), fluorophore-assisted carbohydrate electrophoresis (FACE) (see, e.g., Callewaert et al. (2001) Glycobiology 11(4):275-281 and Freire et al. (2006) Bioconjug. Chem. 17(2):559-564, the disclosures of each of which are incorporated herein by reference in their entirety). Methods for detecting SUMOylation or ubiquitination can include, e.g., mass spectrometry and immunoassays. Immunoassays generally involve the use of an antibody (e.g., a detectably-labeled antibody) that specifically binds to a modification (e.g., a phosphate, glycan, SUMO, or ubiqutin or polyubiquitin modification).

(ii) The disclosure also features a variety of methods and compositions useful for detecting one or more analytes in a mixture, which methods includes the steps of: conjugating an iminobiotin marker to one or more analytes in a mixture; contacting the one or more iminobiotin marker-conjugated analytes to a plurality of analyte-capturing agents, wherein the plurality comprises at least two different analyte-capturing agents, and wherein each of the at least two different analyte-capturing agents specifically bind to a different analyte; and contacting the iminobiotin marker-conjugated analytes with a detectable biotin-binding molecule, wherein the binding of the detectable biotin-binding molecule to an iminobiotin marker-conjugated analyte indicates the presence of the analyte in the mixture. The analytes, detectable biotin-binding molecules, and mixtures can be any of those described herein. Methods for conjugating an iminobiotin marker to an analyte are described above.

In some embodiments, the analyte-capturing agents can be, e.g., an antibody that specifically binds to a target analyte of interest. Where the analyte is a receptor, the analyte-capturing agent can be, e.g., a ligand for the receptor. Likewise, where the analyte is a ligand, the analyte-capturing agent can be a receptor for the ligand. In some embodiments, where the analyte forms a homodimer (or homo-multimer), the analyte-capturing agent can be the analyte itself.

The plurality of analyte-capturing agents can be bound to a solid support such that each analyte-capturing agent can be identified by its position. Exemplary protein-based arrays, and method of making the arrays are described in, e.g., U.S. Publication Nos. 20060040377 and 20050053954 and PCT Publication Nos. WO 04/005477 and WO 06/131687, the disclosures of each of which are incorporated herein by reference in their entirety).

The plurality of analyte-capturing agents can also be conjugated to solid support particles. Many suitable solid support particles are known in the art and illustratively include, e.g., particles, such as Luminex®-type encoded particles, magnetic particles, and glass particles.

Exemplary particles that can be used can have a variety of sizes and physical properties. Particles can be selected to have a variety of properties useful for particular experimental formats. For example, particles can be selected that remain suspended in a solution of desired viscosity or to readily precipitate in a solution of desired viscosity. Particles can be selected for ease of separation from sample constituents, for example, by including purification tags for separation with a suitable tag-binding material, paramagnetic properties for magnetic separation, and the like.

In some embodiments, encoded particles are used. Each particle includes a unique code (such as a bar code, luminescence code, fluorescence code, a nucleic acid code, and the like). Encoding can be used to provide particles for evaluating different analytes in a single biological sample. The code is embedded (for example, within the interior of the particle) or otherwise attached to the particle in a manner that is stable through binding and analysis. The code can be provided by any detectable means, such as by holographic encoding, by a fluorescence property, color, shape, size, weight, light emission, quantum dot emission and the like to identify particle and thus the capture probes immobilized thereto. Encoding can also be the ratio of two or more dyes in one particle that is different than the ratio present in another particle. For example, the particles may be encoded using optical, chemical, physical, or electronic tags. Examples of such coding technologies are optical bar codes fluorescent dyes, or other means. In some embodiments, the particle code is a nucleic acid, e.g., a single stranded nucleic acid.

Different encoded particles can be used to detect or measure multiple analytes (e.g., proteins) in parallel, so long as the encoding can be used to identify the analyte on a particular particle, and hence the presence or amount of the analyte being evaluated. A sample can be contacted with a plurality of such coded particles. When the particles are evaluated, e.g., using a fluorescent scanner, the particle code is read as is the fluorescence associated with the particle from any probe used to evaluate modification of the intact substrate associated with the particles.

One exemplary platform utilizes mixtures of fluorescent dyes impregnated into polymer particles as the means to identify each member of a particle set to which a specific capture probe has been immobilized. Another exemplary platform uses holographic barcodes to identify cylindrical glass particles. For example, Chandler et al. (U.S. Pat. No. 5,981,180) describes a particle-based system in which different particle types are encoded by mixtures of various proportions of two or more fluorescent dyes impregnated into polymer particles. Soini (U.S. Pat. No. 5,028,545) describes a particle-based multiplexed assay system that employs time-resolved fluorescence for particle identification. Fulwyler (U.S. Pat. No. 4,499,052) describes an exemplary method for using particle distinguished by color and/or size. U.S. Publication Nos. 2004-0179267, 2004-0132205, 2004-0130786, 2004-0130761, 2004-0126875, 2004-0125424, and 2004-0075907 describe exemplary particles encoded by holographic barcodes.

U.S. Pat. No. 6,916,661 describes polymeric microparticles that are associated with nanoparticles that have dyes that provide a code for the particles. The polymeric microparticles can have a diameter of less than one millimeter, e.g., a size ranging from about 0.1 to about 1,000 micrometers in diameter, e.g., 3-25 μm or about 6-12 μm. The nanoparticles can have, e.g., a diameter from about 1 nanometer (nm) to about 100,000 nm in diameter, e.g., about 10-1,000 nm or 200-500 nm.

The method can also include the step of: (i) removing the biotin-binding molecule from the iminobiotin marker-conjugated analyte under acidic conditions that decrease the binding affinity of the biotin-binding molecule to iminobiotin or (ii) determining if one or more of the analytes are modified, which methods are described above.

Kits

Also featured herein are kits for use in detecting, isolating, and/or analyzing an analyte in a mixture. The kits can include an iminobiotin marker; a detectable biotin-binding molecule; and instructions for conjugating an iminobiotin marker to an analyte. The kits can also contain one or more solutions for removing a biotin-binding molecule from an iminobiotin marker-conjugated analyte (e.g., an iminobiotin marker-conjugated analyte in a separation matrix) and, optionally, instructions for removing a biotin-binding molecule from an iminobiotin marker-conjugated analyte. At least one of the one or more solutions for removing a biotin-binding molecule from an iminobiotin marker-conjugated analyte can have an acidic pH or contain an unconjugated biotin or iminobiotin marker. The iminobiotin marker can be NHS-iminobiotin or a derivative thereof.

In some embodiments, the kits can include one or more solutions for labeling an iminobiotin marker-conjugated analyte (e.g., in a separation matrix) with a detectable biotin-binding molecule. The one or more solutions can have a basic pH.

In some embodiments, the kits can include instructions for detecting the detectable biotin-binding molecule.

The biotin-binding molecule can be any of those described herein, e.g., neutravidin, captavidin, streptavidin, avidin, or a derivative of any of the foregoing. The biotin-binding molecule can be conjugated to a detectable label. For example, the detectable label can be enzymatically active, fluorescent, calorimetric, and/or luminescent.

In some embodiments, the kit can include iminobiotinylated or biotinylated molecular weight markers and/or a control analyte (or, e.g., two or more, three or more, four or more, five or more, or six or more control analytes). The control analyte can be conjugated to an iminobiotin marker or not conjugated to an iminobiotin-marker. The control analyte can be, e.g., polypeptides such as serum albumin (bovine or human serum albulin).

In some embodiments, the kits can contain one or more buffers. For example, the kits can contain at least one buffer with a basic pH and/or at least one buffer with an acidic pH.

In some embodiments, any of the buffers or solutions included in the kits do not contain detectable levels of primary amines, e.g., as determined by Bradford assay.

In some embodiments, the kits can also contain an amino acid, e.g., a solution containing an amino acid. The amino acid can be, e.g., glycine.

In some embodiments, the kits can also, optionally, include one or more of the following: dimethylsulfoxide (DMSO); PBS; a centrifuge (e.g., a microcentrifuge); one or more polyacrylamide gels (or mini-gels); gel-electrophoresis buffers; a protein dye such as SYPRO® Ruby protein gel stain (PerkinElmer), silver stain (silver nitrate), or colloidal Coomassie blue; fluorescent (or, e.g., luminescent or radiolabeled) gel imaging system and/or computer software for analyzing the gels; biotin-binding reagents (e.g., avidin or streptavidin-based chromatographic support such as a High Capacity Streptavidin Coated plate (PerkinElmer); one or more reagents for preparing a cell lysate from a cell sample and/or fractionating a cell lysate (e.g., the Cellular Protein Fractionation Kit (PerkinElmer catalogue No. PRD101A001KT); and/or one or more reagents for detecting total protein concentration in a mixture (e.g., EZQ™ Protein Quantitation Kit (Invitrogen, Carlsbad, Calif.).

The following example is intended to illustrate, not limit, the invention.

EXAMPLE

Plasma membrane proteins, such as G protein-coupled and tyrosine kinase receptors represent important members of the "druggable" proteome. Defining the complement of plasma membrane proteins displayed on living cells is crucial to discovering diagnostic disease biomarkers, therapeutic agents and drug receptor candidates. In this example, a modified affinity tagging procedure was employed to selectively label cell surface proteins with iminobiotin. A high yield method relying upon detergents to sequentially extract proteins from small numbers of starting material was then employed to fractionate eukaryotic cells on a physiochemical basis into four distinct protein fractions: cytosolic, plasma membrane plus organelle, soluble nuclear, and cytoskeletal plus nuclear matrix. With adherent cells, the sequential extraction is performed directly in the tissue culture dish without removing the cells. At each step of the extraction procedure the insoluble cellular fractions remained attached to the plate, until the appropriate extraction reagent was applied. For suspension-grown cells, extraction started with gentle sedimentation and washing of the cells. The stepwise extraction delivered all four protein fractions from a single specimen. Extracellularly-exposed plasma membrane proteins from the fractions were then selectively visualized using a rhodamine-labeled avidin conjugate after polyacrylamide gel electrophoresis and subsequently protein bands of interest were de-stained prior to trypsinization, followed by matrix assisted laser desorption/ionization-time of flight-mass spectrometry (MALDI-TOF-MS)-based peptide mass fingerprinting or tandem mass spectrometry-based peptide sequencing.

For these studies, the following methods were used.

Confluent (90-95%) HEK 293 Bouvier cells were prepared in T75 cm2 flasks. For Jurkat cells that were grown in suspension, 1×107 cells per milliliter of the imminobiotin solution were used. Cells were washed twice with phosphate buffered saline (PBS). 1.5-1.8 mg iminobiotin (Pierce Chemical, Rockland, Ill.) dissolved in 20 microliters of DMSO was added to 10 ml of PBS and then was added to 1 ml of cells suspended PBS. This resulted in the iminobiotinylation of extracellularly facing plasma membrane proteins.

The flasks were placed on rocking platform or orbital shaker and gently agitated for 60 minutes. The reaction was stopped (quenched) by the addition of 2 ml of 100 mM glycine in PBS. The plasma membrane fraction from the cells was then isolated using "ProteoExtract Native Membrane Extraction Kit" (Calbiochem Cat. No. 444810) according to manufacturer's instructions (Calbiochem, San Diego, Calif.).

The iminobiotinylated plasma membrane fraction was then resolved by SDS-PAGE (SDS-polyacrylamide gel electrophoresis). Next, the gel was fixed in 50% isopropanol in water. The staining buffer was made by adding 1 ml of avidin-Rhodamine (American Qualex, San Clemente, Calif.) stock solution into 99 ml of dilution buffer (10 mM Ammonia Carbonate pH 10.5, 1:100 ratio).

After 15-30 minutes in the fixing buffer, the fixing solution (50% isopropanol in water) was poured off, the gel was rinsed 2-3 times with water and then totally submerged into the staining buffer. The gel in solution was placed on an orbital shaker and gently agitated overnight at room temperature.

The next day, the staining buffer was removed. After rinsing the gel two times in dilution buffer (10 mM Ammonia Carbonate pH 10.5) for 30 minutes, the gels were imaged using a ProXPRESS 2D imaging workstation (PerkinElmer). The stain was optimally detected using a 540 nm excitation source and a 590 nm emission filter.

After imaging, the gel is washed in water five minutes. After the water was removed, the gel was completely submerged in de-staining buffer (50 mM Ammonia Acetate, 0.5 M NaCl, 2 mM d-Biotin, pH 4.0). The gel was placed on orbital shaker and gently agitated between three hours to overnight at room temperature. The gel was imaged again using the same imaging device, in order to verify destaining (removal of the detectable biotin-binding molecule).

The destained proteins bands of interest were then subjected to in-gel trypsinization. Proteins of interest were identified by matrix assisted laser desorption/ionization-time of flight-mass spectrometry (MALDI-TOF-MS)-based peptide mass fingerprinting or by tandem mass spectrometry-based peptide sequencing.

Overall, combining the labeling procedure with the fractionation procedure improved detection of low abundance plasma membrane proteins and allowed monitoring of changes in their association with the underlying cytoskeleton.

The outlined labeling and detection workflow described above should be suitable for the characterization of, inter alia, membrane proteins by a variety of standard gel-based proteomics methods.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What we claim is:

1. A method for isolating an analyte from a mixture, the method comprising:
    providing a mixture comprising an iminobiotin marker-conjugated analyte;
    separating the iminobiotin marker-conjugated analyte from the mixture using a separation matrix;
    labeling the iminobiotin marker-conjugated analyte in the separation matrix with a detectable biotin-binding molecule, wherein the labeling occurs under conditions sufficient for the biotin-binding molecule to bind to iminobiotin with high affinity;
    isolating the iminobiotin marker-conjugated analyte from the separation matrix; and
    removing the detectable biotin-binding molecule from the iminobiotin marker-conjugated analyte under conditions that decrease the binding affinity of the biotin-binding molecule for iminobiotin.

2. The method of claim 1, wherein the mixture comprises more than one iminobiotin marker-conjugated analyte.

3. A method for isolating an analyte from a mixture, the method comprising:
    conjugating an iminobiotin marker to an analyte in a mixture;
    separating the iminobiotin marker-conjugated analyte from the mixture using a separation matrix;
    labeling the iminobiotin marker-conjugated analyte in the separation matrix with a detectable biotin-binding molecule, wherein the labeling occurs under conditions sufficient for the biotin-binding molecule to bind to iminobiotin with high affinity;
    isolating the iminobiotin marker-conjugated analyte from the separation matrix; and
    removing the detectable biotin-binding molecule from the iminobiotin marker-conjugated analyte under conditions that decrease the binding affinity of the biotin-binding molecule for iminobiotin.

4. The method of claim 3, wherein the iminobiotin marker is conjugated to more than one analyte.

5. The method of claim 4, wherein more than one iminobiotin marker-conjugated analyte is isolated from the separation matrix.

6. The method of claim 4, wherein the detectable biotin-binding molecule is removed from more than one iminobiotin marker-conjugated analyte.

7. The method of claim 3, wherein the method comprises: isolating the iminobiotin marker-conjugated analyte from the separation matrix prior to removing the detectable biotin-binding molecule from the iminobiotin marker-conjugated analyte under conditions that decrease the binding affinity of the biotin-binding molecule for iminobiotin.

8. The method of any of claims 3, wherein the method comprises: removing the detectable biotin-binding molecule from the iminobiotin marker-conjugated analyte under conditions that decrease the binding affinity of the biotin-binding molecule for iminobiotin prior to isolating the iminobiotin marker-conjugated analyte from the separation matrix.

9. The method of claim 3, wherein the conditions sufficient for the biotin-binding molecule to bind to iminobiotin with high affinity are basic conditions.

10. The method of any of claims 3, wherein the conditions that decrease the binding affinity of the biotin-binding molecule to iminobiotin are acidic conditions.

11. The method of any of claims 3, wherein the separating comprises resolving the iminobiotin marker-labeled analytes in two dimensions.

12. The method of any of claims 3, wherein the separation matrix is an acrylamide gel.

13. The method of claim 3, further comprising concentrating the iminobiotin marker-conjugated analyte.

14. The method of claim 13, wherein the concentrating occurs before separating the iminobiotin marker-conjugated analyte from the mixture using the separation matrix.

15. The method of claim 14, wherein the concentrating comprises contacting the mixture with a biotin-binding column.

16. The method of claim 3, wherein the detectable biotin-binding molecule is conjugated to a detectable label.

17. The method of claim 16, wherein the detectable label is selected from the group consisting of an enzymatically active label, a fluorescent label, a luminescent label, and a colorimetric label.

18. The method of claim 3, wherein the biotin-binding molecule is selected from the group consisting of neutravidin, captavidin, streptavidin, and avidin.

19. The method of claim 3, wherein the iminobiotin marker-conjugated analyte is a polypeptide.

20. The method of claim 19, wherein the polypeptide is a cell-surface polypeptide.

21. The method of claim 3, further comprising, after separating the iminobiotin marker-conjugated analyte from the mixture using a separation matrix, fixing the iminobiotin marker-conjugated analyte in the separation matrix with a fixing agent.

22. The method of claim 21, wherein the fixing agent is isopropanol.

23. The method of claim 3, further comprising, after labeling the iminobiotin marker-conjugated analyte with a detectable biotin-binding molecule, detecting the iminobiotin marker-conjugated analyte.

24. The method of claim 3, further comprising analyzing the isolated iminobiotin marker-conjugated analyte.

25. The method of claim 24, wherein the analyzing comprises mass spectrometry.

26. The method of claim 24, wherein the analyzing comprises detecting if the iminobiotin marker-conjugated analyte is modified.

27. The method of claim 3, further comprising, after separating the iminobiotin marker-conjugated analyte from the mixture, determining the amount of iminobiotin marker-conjugated analyte.

28. The method of claim 3, wherein the mixture is a cell lysate.

29. The method of claim 3, wherein the iminobiotin marker is conjugated to the one or more analytes at the surface of a cell.

30. The method of claim 29, further comprising after conjugating the iminobiotin marker to the one or analytes, preparing a mixture from the cell.

* * * * *

UNITED STATES PATENT AND TRADEMARK OFFICE
CERTIFICATE OF CORRECTION

PATENT NO.         : 7,879,573 B2                                   Page 1 of 1
APPLICATION NO.    : 11/772739
DATED              : February 1, 2011
INVENTOR(S)        : Wayne Forrest Patton et al.

It is certified that error appears in the above-identified patent and that said Letters Patent is hereby corrected as shown below:

On the Title page, in line 7 under Other Publications, item (56); replace "electroporesis," with --electrophoresis,--.

In column 18, line 56, in claim 8, replace "any of claims" with --claim--.

In column 18, line 65, in claim 10, replace "any of claims" with --claim--.

In column 19, line 1, in claim 11, replace "any of claims" with --claim--.

In column 19, line 4, in claim 12, replace "any of claims" with --claim--.

In column 20, line 27, in claim 30, after "or," insert --more--.

Signed and Sealed this
Twenty-fourth Day of May, 2011

David J. Kappos
*Director of the United States Patent and Trademark Office*